US00PP32087P2

(12) United States Plant Patent
Eveleens et al.

(10) Patent No.: US PP32,087 P2
(45) Date of Patent: Aug. 18, 2020

(54) ***HYDRANGEA* PLANT NAMED 'HOKOMAZONE'**

(50) Latin Name: *Hydrangea macrophylla*
Varietal Denomination: Hokomazone

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 16/602,078

(22) Filed: Aug. 1, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named 'Hokomazone' that is characterized by its mophead inflorescence with sterile flower sepals that are pink in color with tints of green, its sterile flower sepals with a firm substance, its upright plant habit, and its suitability for use both as a potted plant and as a cut flower.

2 Drawing Sheets

Botanical classification: *Hydrangea macrophylla.*
Varietal denomination: 'Hokomazone'.

CROSS REFERENCE TO RELATED APPLICATIONS

This application is related to U.S. Plant Patents for plants derived from the same breeding program that are entitled *Hydrangea* Plant Named 'Hokomathyst' (U.S. Plant Pat. No. 22,261) and *Hydrangea* Plant Named 'Hokomac' (U.S. Plant Pat. No. 22,259) and a U.S. Plant Patent Application entitled *Hydrangea* Plant Named 'Hortmaspoli' (U.S. Plant application Ser. No. 16/602,229.

BACKGROUND OF THE INVENTION

The present invention relates to a new and distinct cultivar of *Hydrangea macrophylla* and will be referred to hereafter by its cultivar name, 'Hokomazone'. 'Hokomazone' represents a new bigleaf *hydrangea*, a perennial shrub grown for landscape use, a container plant, and as a cut flower.

The new cultivar was discovered by the Inventors in August of 2012 as a naturally occurring branch mutation of *Hydrangea* 'Hokomac' (U.S. Plant Pat. No. 22,259) that was growing in a unheated greenhouse in a container in Boskoop, The Netherlands.

Asexual propagation of the new cultivar was first accomplished by stem cuttings by one of the Inventors in August of 2012 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomazone' as a unique cultivar of *Hydrangea macrophylla.*

1. 'Hokomazone' exhibits a mophead inflorescence with sterile flower sepals that are pink in color with tints of green.
2. 'Hokomazone' exhibits sterile flower sepals with a firm substance.
3. 'Hokomazone' exhibits an upright plant habit.
4. 'Hokomazone' exhibits suitability for use both as a potted plant and as a cut flower.

The parent plant of 'Hokomazone' differs from 'Hokomazone' in having pink inflorescences that are darker pink in color with sterile flower sepals with more serrated margins. 'Hokomazone' can be most closely compared to the *Hydrangea macrophylla* cultivars 'Hokomathyst' and 'Hortmaspoli'. 'Hokomathyst' and 'Hortmaspoli' are both similar to 'Hokomazone' in having sterile flower sepals with a firm substance and an upright plant habit. 'Hokomathyst' differs from 'Hokomazone' in having more green coloration on the sterile flower sepals and a flattened shaped inflorescence. 'Hortmaspoli' differs from 'Hokomazone' in having sterile flower sepals that are green in color with pink centers.

BRIEF DESCRIPTION OF THE DRAWINGS

The accompanying colored photographs illustrate the overall appearance and distinct characteristics of the new *Hydrangea*. The photographs were taken of a two-year-old plant of 'Hokomazone' as grown in an unheated greenhouse in a 17-cm container in Boskoop, The Netherlands.

The photograph in FIG. 1 provides a side view of the plant habit of 'Hokomazone' in bloom.

Figure 1:
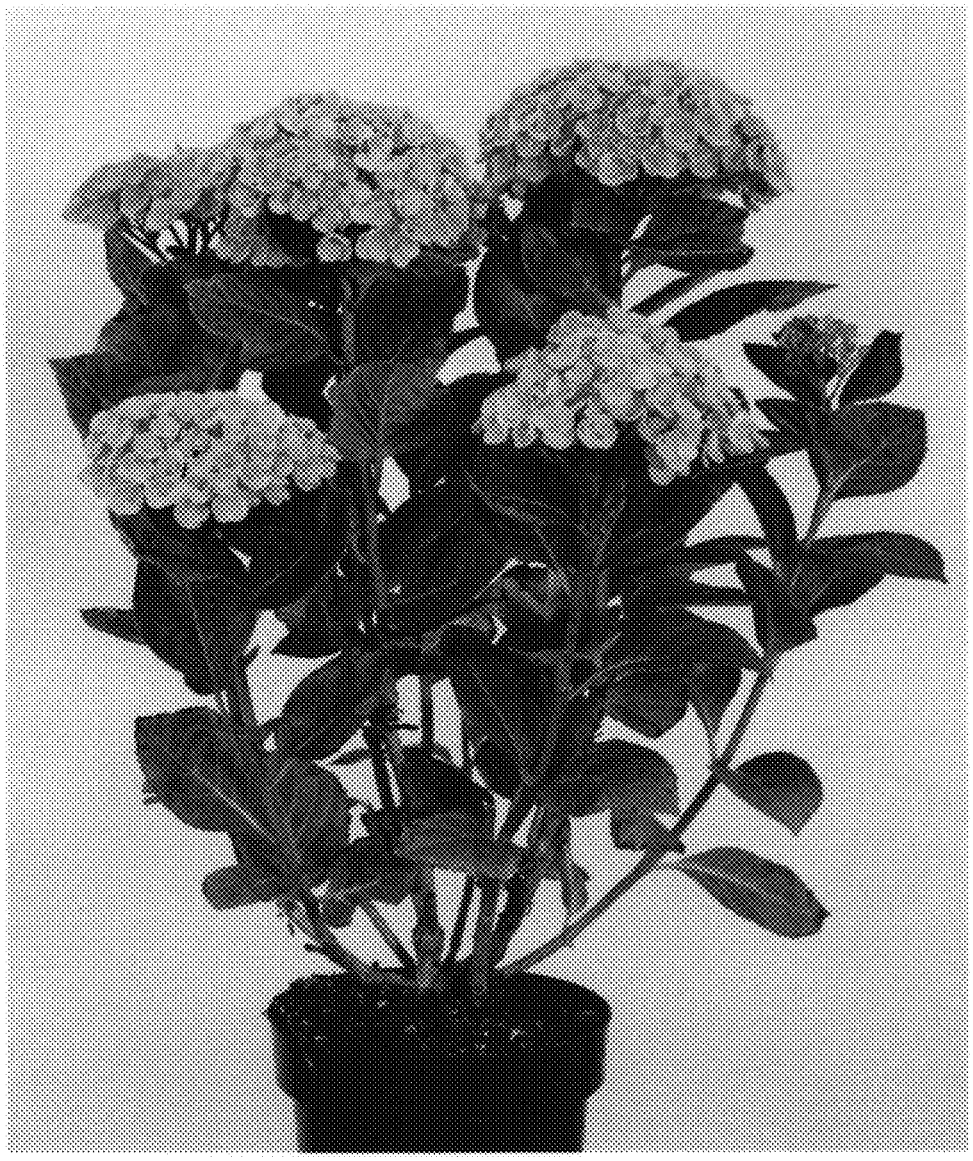
Figure 2:
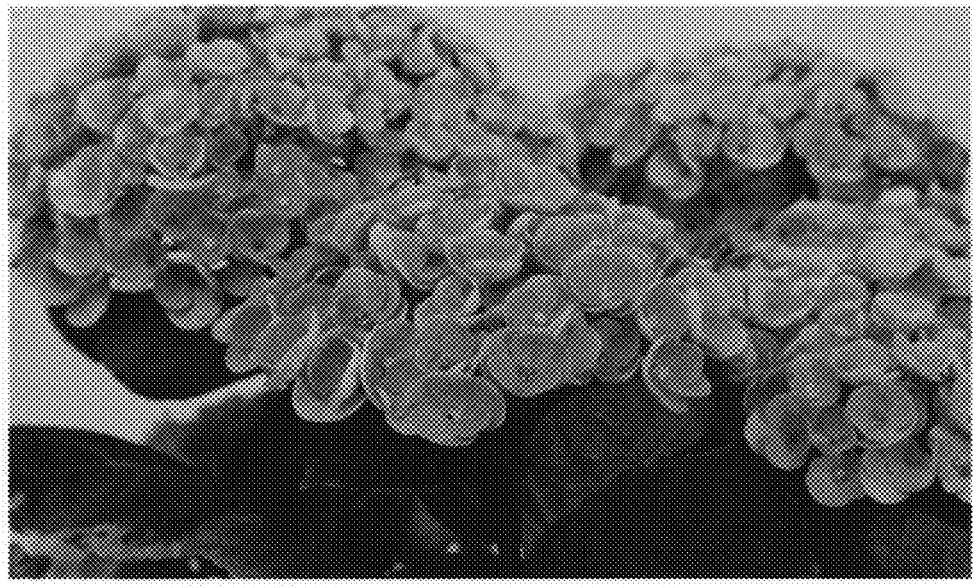

The photograph in FIG. 2 provides a close-up view of fully open inflorescences of 'Hokomazone'.

Figure 3:
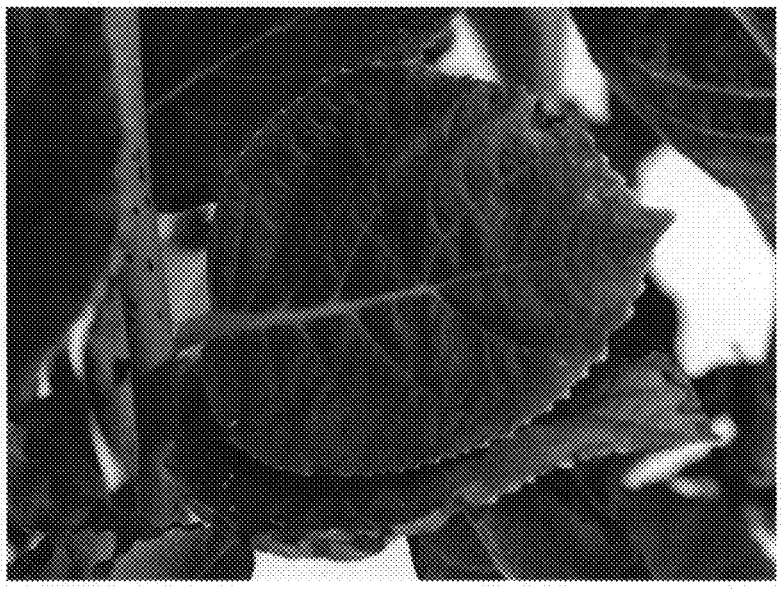

The photograph in FIG. 3 provides a close-up view of the foliage of 'Hokomazone'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'Hokomazone' as grown in an unheated greenhouse in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to late summer with flowers showy in color at least for 2 months in the Netherlands.

*Plant type.*—Deciduous shrub, mophead type *Hydrangea.*

*Plant habit.*—Spreading, upright.

*Height and spread.*—An average of 52.8 cm in in height and 48 cm in spread as grown in a 17-cm container, reaches 1 m in height and spread as a 3-year-old plant in the landscape.

*Hardiness.*—At least U.S.D.A. Zones 5 to 9.

*Diseases and pests.*—No susceptibility and resistance to diseases or pests has been observed.

*Root description.*—Fine and fibrous, 161C in color.

*Propagation.*—Stem cuttings.

*Root development.*—An average of 6 weeks for root initiation with a young rooted plant produced in an average of 18 weeks.

*Growth rate and vigor.*—Moderate.

Stem description:

*Stem shape.*—Rounded.

*Stem strength.*—Strong.

*Stem color.*—Young; 144B, mature; 144A, internodes occasionally tinged with N186C, old bark; 199B to 199C and N199D.

*Stem size.*—An average of 24.8 cm in length (excluding inflorescence) and 7 mm in diameter.

*Stem surface.*—Glabrous, sparsely covered with lenticels that are an average of 1 mm in length and 1 mm in diameter, N186C in color.

*Stem aspect.*—Average angle of 25° to vertical.

*Internode length.*—An average of 6 cm.

*Branching.*—Freely branching with an average of 14 lateral branches.

Foliage description:

*Leaf shape.*—Broad ovate to broad elliptic.

*Leaf arrangement.*—Opposite.

*Leaf division.*—Simple.

*Leaf base.*—Short attenuate.

*Leaf apex.*—Short apiculate.

*Leaf margins.*—Crenate to serrate.

*Leaf venation.*—Pinnate, color; color upper and lower surface 146D.

*Leaf size.*—An average of 10.7 cm in length and 7.6 cm in width.

*Leaf attachment.*—Petiolate.

*Leaf number.*—An average of 8 to 10 per lateral stem.

*Leaf surface.*—Both surfaces; smooth and slightly glossy.

*Leaf color.*—Young foliage; upper surface 137B, lower surface 144A, mature foliage; upper surface 137A, lower surface between 146B and 147B.

*Petioles.*—An average of 1.6 cm in length and 4 mm in diameter, upper and lower surface 145A in color, surface smooth and very slightly glossy on upper surface and smooth and slightly glossy on the lower surface.

Inflorescence description:

*Inflorescence type.*—Terminal panicle, flattened mophead comprised of sterile flowers above fertile flowers.

*Lastingness of inflorescence.*—Sterile flowers; persistent for an average of 6 weeks, fertile flowers; self-cleaning, an average of 3 days.

*Lastingness as a cut flower.*—An average of 2 weeks in color.

*Inflorescence number.*—One per lateral stem.

*Inflorescence size.*—An average of 8.3 cm in height and 15.6 cm in diameter.

*Flower number.*—An average of 120 sterile flowers and 50 fertile flowers per panicle.

*Flower fragrance.*—None.

*Flower aspect.*—Sterile flowers; upright to outward, fertile flowers; upright.

*Flower size.*—Sterile flowers; an average of 1.9 cm in diameter and 9.5 mm in depth, fertile flowers; an average of 6 mm in diameter and 5 mm in depth.

*Flower type.*—Rotate, cup-shaped.

*Flower buds.*—Sterile flowers; an average of 9 mm in length and 1.3 cm in diameter, cup shaped, 145A, fertile flowers; an average of 5 mm in length and 3 mm in diameter, obovate in shape, color; 145A, changing to 145B at the base, tip tinged 54B, immature sepals 144B, slightly tinged 54B at the tip, immature ovary 144B.

*Peduncles.*—Strong, flattened oval in shape, an average of 2 cm in length and 2.3 mm in width on primary peduncles and secondary peduncles 1 cm in length and 1.5 mm in width, 63B in color, surface matte and densely pubescent surface covered with thin pubescence an average of 0.2 mm in length and too small to measure color.

*Pedicels.*—Sterile flowers; held primarily at an average angle of 40°, an average of 2 cm in length and 1 mm in diameter, moderately strong strength, 63B in color, matte and moderately covered with thin pubescence an average of 0.2 mm in length and too small to measure color, fertile flowers; held at an average angle of 25° from vertical, an average of 4 mm in length and 1 mm in diameter, moderate strength, 182D in color, surface matte and slightly covered with thin pubescent hairs an average of 0.2 mm in length and too small to measure color.

*Petals.*—Sterile flowers; an average of 4, rotate, cruciform in arrangement, acute apex, cuneate base, entire margins, ovate to moderately to moderately concave in shape, average of 2.5 mm in length and 1.25 mm in width, both surfaces; smooth, glabrous and matte, color; when opening and fully open upper surface 76A, changing to 76D at the base and margins, when opening and fully open lower surface 76B, changing to 76D at the base and margins, fertile flowers; an average 5, rotate in arrangement, ovate and concave in shape, entire margin, acute apex, cuneate base, an average of 4 mm in length and 2 mm in width, upper and lower surface glabrous and matte, color; upper surface when opening and fully open 76B, changing to 76D at the base, tip and margins, lower surface when opening and fully open 76A, changing to 76D at the base, tip and margins.

*Sepals.*—Sterile flowers; 4, rotate, rounded apex, broadly cuneate base, entire to margins, concave to reniform in shape, an average of 1.3 cm in length and 1.6 cm in width, upper and lower surface glabrous and matte, color; when opening upper surface N66C, when opening lower surface 65A, when fully open upper surface 63B, when fully open lower surface N66D, upper surface changing to 146D, flushed with 70C to 70D at the base, veined 68B to 68C, lower surface changing to 195B, veined 68B to 68C, fertile flowers; an average of 5, ovate in shape, entire margin, acute apex, 1.25 mm in length, 0.75 cm width, and broadly cuneate base, both surfaces are glabrous and matte, color; upper surface when opening 144C, lower surface when opening 144B, slightly tinged 54B at the top, upper and lower surface when fully open 150D.

Reproductive organs:

*Gynoecium.*—Sterile flowers; 2 to 3 pistils, an average of 1.5 mm in length, stigma; club-shaped and NN155A in color, style; 0.5 mm in length, 65C to 65D in color, ovary is N155B in color, fertile flowers; an average of 2 to 3 pistils, an average of 1.5 mm in length, stigma; club-shaped and NN155A in color, style; 0.5 mm in length and 65C to 65D in color, ovary is 159D in color.

*Androecium.*—Sterile flowers; an average of 8 stamens, filaments; an average of 2.25 mm in length and NN155D in color, anthers; broad oblong in shape, an average of 0.5 mm in length and 155D in color, pollen; low in quantity, 155A in color, fertile flowers; an average of 10 stamens, filaments; an average of 3 mm in length and NN155D in color, anthers; broad oblong in shape, an average of 0.5 mm in length and 155D in color, pollen; low in quantity and 155A in color.

*Fruit and seed.*—None observed to date.

It is claimed:

1. A new and distinct cultivar of *Hydrangea* plant named 'Hokomazone' substantially as herein illustrated and described.

* * * * *